United States Patent
Bogue

(10) Patent No.: US 7,163,700 B2
(45) Date of Patent: Jan. 16, 2007

(54) AMORPHOUS DRUG BEADS

(75) Inventor: Beuford Arlie Bogue, Broad Run, VA (US)

(73) Assignee: Capricorn Pharma, Inc., Frederick, MD (US)

( * ) Notice: Subject to any disclaimer, the term of this patent is extended or adjusted under 35 U.S.C. 154(b) by 346 days.

(21) Appl. No.: 10/207,975

(22) Filed: Jul. 31, 2002

(65) Prior Publication Data

US 2003/0026843 A1    Feb. 6, 2003

Related U.S. Application Data

(60) Provisional application No. 60/308,569, filed on Jul. 31, 2001.

(51) Int. Cl.
*A61K 9/16* (2006.01)
*A61K 9/50* (2006.01)

(52) U.S. Cl. ............... 424/491; 424/489; 424/490; 424/492; 424/496; 424/498

(58) Field of Classification Search ............ 424/601, 424/471, 489–496, 488, 498
See application file for complete search history.

(56) References Cited

U.S. PATENT DOCUMENTS

| | | | |
|---|---|---|---|
| 4,540,602 A | 9/1985 | Motoyama et al. | 427/213.31 |
| 5,118,528 A | 6/1992 | Fessi et al. | 427/213.36 |
| 5,246,707 A | 9/1993 | Haynes | 424/450 |
| 5,858,410 A | 1/1999 | Muller et al. | 424/489 |
| 6,395,300 B1 | 5/2002 | Straub et al. | 424/489 |

FOREIGN PATENT DOCUMENTS

| | | |
|---|---|---|
| WO | WO 9744014 A1 * | 11/1997 |
| WO | WO 98/57967 | 12/1998 |
| WO | WO 9857967 A1 * | 12/1998 |

* cited by examiner

*Primary Examiner*—Michael G. Hartley
*Assistant Examiner*—Micah-Paul Young
(74) *Attorney, Agent, or Firm*—Thorpe North & Western LLP

(57) ABSTRACT

The present inventive subject matter relates to amorphous drug beads comprising an amorphous active drug and an organic surfactant having improved solubility, absorption and wettability characteristics. The present inventive subject matter further relates to methods of preparing the amorphous drug beads, wherein molten drug beads are subject to a cooling step with or without shear.

9 Claims, 1 Drawing Sheet

Dissolution of Amorphous Itraconazole vs crystalline Itraconazole

AMORPHOUS DRUG BEADS

U.S. Provisional Patent Application(s) No. 60/308,569 filed Jul. 31, 2001.

BACKGROUND OF THE INVENTION

1. Field of the Invention

The present inventive subject matter relates to amorphous drug beads comprising an amorphous active drug and an organic surfactant having improved solubility, absorption and wettability characteristics. The present inventive subject matter further relates to methods of preparing the amorphous drug beads, wherein molten drug beads are subject to a cooling step with or without shear.

2. Description of the Related Art

Over the years, compositions and methods have been developed to achieve improved delivery of a therapeutically effective amount of a drug. In particular, compositions and methods providing enhanced solubility, absorption and wettability characteristics of a drug, resulting in a desired dissolution rate in vivo, have been sought.

Among the reasons for the increased focus in this field of art are the poor solubility characteristics of new pharmaceuticals. Many newly developed active drugs possess poor absorption profiles and unfavorable dissolution characteristics. A cursory review of pharmacokinetic characteristics of several recently developed active drugs suggests that more than 40% of these drug substances have an aqueous solubility below 1 mg/ml, while 32% have an aqueous solubility below 0.1 mg/ml. The low solubility of these active drugs in water and in organic solvents translates into a lowered ability to deliver the drug to an animal in need thereof.

For example, potential absorption problems may occur via the oral route of administration unless the active substance has an aqueous solubility above 10 mg/ml over a pH range of 1–7. Pharmacological testing is also hampered since, following oral or intramuscular administration, it is not possible to test the bioavailability of an active drug due to its low solubility. Accordingly, the implementation of absorption enhancing methods is currently a major field of research in formulating and developing drug dosage forms.

One known method for overcoming the problems of a low dissolution rate of an active drug is to reduce the particle size of the drug, thereby causing the surface area available for interaction with the fluids to be significantly increased. For drugs where absorption is limited by dissolution rate, particle size reduction clearly represents a viable means for increasing bioavailability. In particular, the dissolution rate of a drug increases as the particle surface area increases in accordance with the Noyes-Whitney law. This causes an increase in the rate of flooding of active compounds, and the maximum plasma level is reached faster (e.g. oral or i.v. administration of micro- and nano-particulate drug crystals). Aqueous solubility of active drug substances is also improved by particle size reduction.

One advantage to thusly reducing the particle size of active drugs is that intravenous administration of insoluble or sparingly soluble active drugs can be accomplished. Moreover, sparingly soluble active drugs can be injected without blockade by blood capillaries.

Another advantage is a reduction in the injection volume of active drugs. For example, if water-solubility is low, a relatively large volume is administered. Alternatively, if micro- and nano-particulate drug crystals of a reduced size are used, they can be dispersed to form a saturated solution of the active compound, thereby reducing the volume of the injection.

Small particle drugs can also more readily be employed for controlled drug delivery. For example, after oral administration, oral immunization could take place via the M cells in the gastrointestinal tract, and selective concentration in the absorption windows of the gastrointestinal tract could be achieved via bioadhesives.

Another use for small particle active drugs is drug targeting. After intravenous injection, it is well known in the art that particles accumulate specifically in certain organs, e.g. liver, spleen, or bone marrow, as a function of their surface properties. Therefore, after administration, particle accumulation in targeted organs can be achieved. Targeted accumulation of the active compound at the site of action reduces side effects and increases therapeutic efficiency.

Accordingly, many techniques have been developed to reduce the particle size of an active drug to take advantage of these beneficial properties. The majority of these techniques relate to various milling techniques wherein the active drug is comminuted by dry grinding techniques and subsequent fractionation. However, these milling techniques have a significant disadvantage of loss of the active compound during the milling process. Sometimes the milling process may waste more than 90% of the active compound, thereby greatly reducing cost effectiveness.

One known milling technique attempts to circumvent this loss by providing for a high molecular weight polymer which provides a higher processing temperature and a longer period for the manipulation of a resin and drug in a mill or other processing machine. These conditions increase the amount of active drug that can be dissolved in the resin without degrading the resin, and the relative rigidity of the resin can assist in the grinding to form granular particles or powders of the active drug.

In this regard, U.S. Pat. No. 5,246,707, the contents of which are herein incorporated by reference in their entirety, describes surfactant-stabilized micro-particles, which may additionally comprise iron particles within the micro-particles, in order to allow location of the particles via magnetic fields.

Further, U.S. Pat. No. 4,540,602, the contents of which are herein incorporated be reference in their entirety, describes a process for the preparation of micro- and nano-particulate drug crystals by wet grinding. U.S. Pat. No. 5,145,684, the contents of which are herein incorporated by reference in their entirety, additionally describes wet grinding of active drugs with a pearl mill. A further reduction in the particle size provided by such mills is possible if the viscosity of the dispersion medium is increased while the speed of rotation remains constant.

However, the above outlined milling techniques have the disadvantages of not being amenable to industries of scale and result in relatively large particles. Moreover, the techniques are only applicable to certain classes of molecules and do not ensure homogenous results.

One technique to overcome these disadvantages is to produce the active drug suspensions by precipitation. European Patent Application No. 0 275 796 A1, the contents of which are herein incorporated by reference in their entirety, discloses the preparation of a liquid phase consisting of a solution of an active drug added to a second liquid phase consisting of a non-solvent or a mixture of non-solvents of the active drug to which one or more surfactants may be added, wherein both phases are mixed with moderate agitation to produce a colloidal suspension of particles of the active drug. The non-solvent or the mixture of non-solvents for the active drug is miscible in all proportions with the solvent or mixture of solvents for the active drug.

However, the disadvantage of this technique is that its effectiveness is limited to substances sufficiently soluble in water or a given solvent.

Accordingly, there remains a need for a composition and method which achieves improved delivery of a therapeutically effective amount of an active drug without providing any of the disadvantages noted above.

U.S. Pat. No. 5,858,410, the contents of which are herein incorporated by reference in their entirety, attempts to sidestep the problem of insoluble or sparingly soluble drugs by avoiding a precipitation technique. In particular, this patent discloses that active drugs with a low solubility can have an increased dissolution rate by using an ultrasonic probe, a ball mill, or a pearl mill, wherein the drug is comminuted by using cavitation or shearing and impact forces, with introduction of a high amount of energy, without prior conversion into a melt.

However, a disadvantage of this milling technique is that the residual content of solvents in the product can only be removed with great difficulty, delaying crystallization and often producing a high proportion of large particles.

Moreover, recent investigations directly contravene the teachings of this patent by suggesting that crystals derived from a melt give rise to significant advantages over crystals derived from milling. In particular, crystals co-precipitated out of a melt are significantly less irritating than the solid dispersions created by milling (Khan, Shojael, Karnachi and Keddy, "Comparative Evaluation of Controlled-Release Solid Oral Dosage Forms Prepared with Solid Dispersions and Co-precipitates", Pharmaceutical Technology, May 1999). These recent investigations further provide in vivo ulcerogenicity data clearly indicating that drugs co-precipitated from a melt produce less gastric irritation than drug dispersions created by milling.

However, no known methods provide an acceptable active dosage form produced from a melt comprising an amorphous active drug and an organic surfactant wherein the organic surfactant coats the amorphous active drug.

Accordingly, there is a need for amorphous active drug products having improved solubility, absorption, and wettability characteristics, and for processes to manufacture such drug products easily and reliably.

SUMMARY OF THE INVENTION

The present inventive subject matter relates to an amorphous drug bead comprising: an amorphous active drug; and an organic surfactant adsorbed on the surface of said amorphous active drug, wherein said amorphous active drug is in a non-crystalline form and is insoluble in and not miscible with said surfactant; wherein said organic surfactant completely coats and does not chemically bond with said amorphous active drug; and wherein said amorphous drug bead has a particle size of about 90 nm to about 50 microns.

In a preferred embodiment, the present inventive subject matter additionally relates to a method of making an amorphous drug bead, the method comprising: a) providing an amorphous active drug; b) melting said amorphous active drug; c) forming a droplet from said melted amorphous active drug; and d) quenching said droplet in a liquid organic surfactant; wherein said droplet immediately solidifies when quenched in said liquid organic surfactant, said liquid organic surfactant having a lower melting point than said amorphous active drug; wherein said amorphous drug bead has a particle size of about 1 to about 50 microns.

In another preferred embodiment, the present inventive subject matter further relates to a method of making an amorphous drug bead, the method comprising: a) providing an amorphous active drug and a molten organic surfactant; b) melting said amorphous active drug in the presence of said molten organic surfactant; c) allowing said melted amorphous active drug and said molten organic surfactant to form two phases; d) subjecting said two phases to high shear to form an emulsion; and e) quenching said emulsion to solidify said amorphous active drug; wherein said melted amorphous active drug is insoluble in and not miscible with said melted organic surfactant; wherein said amorphous drug bead has a particle size of about 90 nm to about 10 microns.

BRIEF DESCRIPTION OF THE DRAWING

The invention may be better understood by reference to the accompanying drawing wherein.

DETAILED DESCRIPTION OF THE INVENTION

Figure 1:
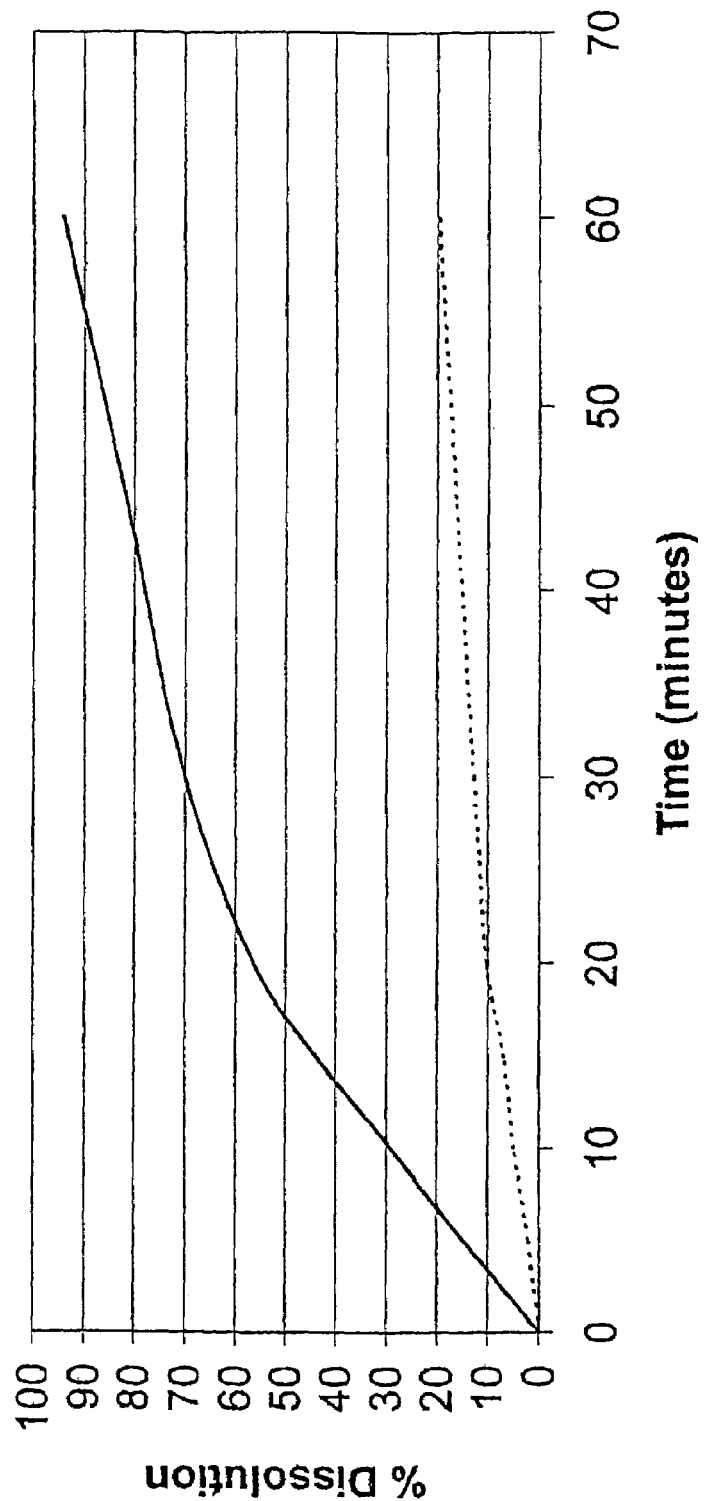
FIG. 1 is a graphical representation of dissolution rates plotted as percent dissolution versus time, comparing amorphous Itraconazole to crystalline Itraconazole.

As used herein, the term "solubility" refers to the amount of a substance that can be dissolved in a given amount of solvent.

As used herein, the term "absorption" refers to the process of drug movement from the site of administration toward the systemic circulation.

As used herein, the term "wettability" refers to the ability of a substance to have intimate surface contact with a liquid.

As used herein, the term "amorphous" is to be understood as the non-crystalline state of a substance, which has no molecular lattice structure.

As used herein, the term "particle size" refers to a number average particle size as measured by conventional particle size measuring techniques well known to those skilled in the art, such as but not limited to sedimentation field flow fractionation, photon correlation spectroscopy, or disk centrifugation.

As used herein, "room temperature" refers to a temperature at or around 25° C.

The term "pharmaceutically-acceptable carrier" as used herein means one or more compatible solid or liquid filler, diluants, or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with each other in a manner such that there is no interaction which would substantially impair the desired pharmaceutical efficacy. Examples of such carriers include gels, liquid suspensions, emulsions, creams, ointments, powders, solutions, and lotions.

Generally, the present inventive subject matter relates to amorphous drug beads having improved solubility, absorption, and wettability characteristics. The present inventive subject matter further relates to a method of preparing these amorphous drug beads wherein a molten drug bead is subject to a coating step with or without shear.

The amorphous drug bead comprises an amorphous active drug and an organic surfactant. In its melted state, the amorphous active drug is essentially insoluble and not miscible with the organic surfactant. Additionally, the amorphous active drug does not chemically bond with the organic surfactant; rather, the organic surfactant is physically attached to the surface of the amorphous active drug. The amorphous drug beads are formed while quenching the melted amorphous active drug together with the organic surfactant.

The amorphous active drug of the final amorphous drug beads is at least partially covered or coated with an organic surfactant. In a preferred embodiment, the amorphous drug beads are completely coated with the organic surfactant.

The amorphous drug beads of the present inventive subject matter are preferably flowable, which makes it easy to pack them in appropriate containers.

The present inventive subject matter can be practiced with a wide variety of amorphous active drugs. The active drugs preferably are present in an essentially pure form. The active drugs can be poorly or sparingly soluble and dispersible in at least one liquid medium. By "poorly or sparingly soluble" it is meant that the active drugs have a solubility in the liquid dispersion medium of less than about 100 mg/ml, and preferably of less than about 1 mg/ml. A preferred liquid dispersion medium is water. However, the present inventive subject matter can be practiced with other liquid media in which an active drug is poorly soluble and dispersible including, for example, aqueous salt solutions, safflower oil, and solvents such as ethanol, t-butanol, hexane, and glycol. The pH of the aqueous dispersion media can be adjusted by techniques well known to those of skill in the art.

Suitable active drugs which are useful in the present amorphous drug beads can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines. Preferred active drugs include those intended for oral administration and intravenous administration. A description of these classes of drugs and a listing of species within each class can be found in Martindale, *The Extra Pharmacopoeia*, 29th Edition, The Pharmaceutical Press, London, 1989, the disclosure of which is hereby incorporated by reference in its entirety. These active drugs are commercially available and/or can be prepared by techniques well known to those of skill in the art.

4-[4-[4-[4-[[2-(2,4-Dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one (Itraconazole) or a pharmaceutically acceptable salt thereof is a particularly preferred amorphous active drug which can be used according to the present inventive subject matter as described herein.

The amorphous drug beads of the present inventive subject matter contain a discrete phase of an amorphous active drug as described above having an organic surfactant adsorbed on the surface thereof. Useful organic surfactants are believed to include those which physically adhere to the surface of the active drug but do not chemically bond to the drug.

Preferred organic surfactants include nonionic and anionic surfactants. Suitable organic surfactants can preferably be selected from the group consisting of polymers, low molecular weight oligomers, natural products, gelatin, casein, lecithin (phosphatides), gum acacia, cholesterol, tragacanth, stearic acid, benzalkonium chloride, calcium stearate, glyceryl monostearate, cetostearl alcohol, cetomacrogol emulsifying wax, sorbitan esters, polyoxyethylene alkyl ethers, macrogol ethers such as Cetomacrogol 1000, polyoxyethylene castor oil derivatives, polyoxyethylene sorbitan fatty acid esters e.g. the commercially available Tweens™, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethyicellulose, hydroxypropylcellulose, hydroxypropylmethycellulose phthalate, noncrystalline cellulose, magnesium aluminum silicate, triethanolamine, polyvinyl alcohol, polyvinylpyrrolidone (PVP), dextran, lecithin, organic solvents, and mixtures thereof. Most of these excipients are described in detail in the *Handbook of Pharmaceutical Excipients*, published jointly by the American Pharmaceutical Association and The Pharmaceutical Society of Great Britain, The Pharmaceutical Press, 1986, the disclosure of which is hereby incorporated by reference in its entirety. These surface modifiers are commercially available and/or can be prepared by techniques known in the art.

Preferred organic surfactants useful according to the present inventive subject matter include polyvinyl alcohol, polyethylene glycol ("PEG"), polyvinyl pyrrolidone, Pluronic™ F68 and F108 which are block copolymers of ethylene oxide and propylene oxide (available from BASF), Tetronic™ 908 which is a tetrafunctional block copolymer derived from sequential addition of ethylene oxide and propylene oxide to ethylenediamine (available from BASF), dextran, lecithin, Aerosol™ OT which is a dioctyl ester of sodium sulfosuccinic acid (available from American Cyanamid), Duponol™ P which is a sodium lauryl sulfate (available from DuPont), Triton™ X-200 which is an alkyl aryl polyether sulfonate (available from Rohm and Haas), Tween™ and Tween™ 80 which are polyoxyethylene sorbitan fatty acid esters (available from ICI Specialty Chemicals), and Carbowax 3350 and 934 which are polyethylene glycols (available from Union Carbide). Surface modifiers which have found to be particularly useful according to the present inventive subject matter include polyvinylpyrrolidone, Pluronic™ F-68, and lecithin.

It should be noted that when used according to the present inventive subject matter, the organic surfactants should not chemically react with the amorphous active drug to avoid drug interactions.

The amorphous drug beads of the present inventive subject matter have a particle size of about 90 nm to about 50 microns. With reference to the effective average particle size, it is preferred that at least 50% and, more preferably, at least 75% of the particles have a particle size less than the effective average.

The amorphous drug beads of the present inventive subject matter can be made by a variety of devices which provide sufficiently high shear for shear mixing, if desired. There are a large variety of these devices available on the market readily ascertainable by one of skill in the art for the intended purpose of the present inventive subject matter.

A first method for making the amorphous drug beads of the present inventive subject matter comprises the steps of providing an amorphous active drug; melting the amorphous active drug; forming a small droplet from said melted amorphous active drug; and quenching the droplet in a bath of molten/liquid organic surfactant. The molten organic surfactant must have a lower melting point than the molten droplet, so that the droplet will immediately solidify when dropped into the organic surfactant. This method will result in beads of the amorphous active drug coated by the organic surfactant, or surface active agent.

Typically, the amorphous active drug should not decompose at its melting point, allowing the drug to be melted before addition to the molten organic surfactant. For stability reasons, the organic surfactant should have a melting point above room temperature, preferably above 40° C. This method will typically produce amorphous drug beads having a particle size of about 1 to about 50 microns. In a preferred embodiment, the method produces amorphous drug beads having a particle size of about 5 to about 45 microns.

A second method for making the amorphous drug beads of the present inventive subject matter comprises the steps of providing an amorphous active drug and a molten organic surfactant; melting the amorphous active drug in the present of said molten organic surfactant; allowing said melted amorphous active drug and said molten organic surfactant to form two phases; subjecting said two phases to high shear to form an emulsion; and quenching said emulsion to solidify said amorphous active drug. During quenching, amorphous drug beads are formed, which are coated with the organic surfactant.

Typically, any equipment generating high shear which can be used for emulsification and withstand the required temperatures is applicable according to this method. Typically, the amorphous active drug is not miscible with and either insoluble in or slightly soluble in the molten organic surfactant. The emulsion must be quenched quickly to solidify the drug in its amorphous state. This method will typically produce amorphous drug beads having a particle size of about 90 nm to about 10 microns. In a preferred embodiment, the method produces amorphous drug beads having a particle size of about 100 nm to about 5 microns.

One of ordinary skill in the art will understand that the particular theory of the invention is not limited to any single one of the above theories, or may be a combination of the above theories or involve theories as of yet not ascertainable and do not limit in any way the ability to practice the invention as disclosed herein.

Compositions and methods for the preparation of the present inventive amorphous drug beads will be readily apparent to those skilled in the art, in view of the present disclosure, when the present disclosure is coupled with information known in the art.

It should be recognized by one of skill in the art that the drug product described herein might be a solid product that is amorphous and may be flowable. Such products may be conveniently processed by techniques well known in the art to form products having sizes of about 16 mesh. This enables incorporation of the present inventive amorphous drug beads into various pharmaceutical delivery system(s). These delivery systems can be independently selected from the group consisting of tablets, bi-layer tablets, capsules, gelatin capsules, caplets, lozenges, chewable lozenges, beads, powders, granules, dispersible granules, cachets, patches, particle inhalants, implants, ingestibles, injectable or infuseables.

The present inventive subject matter also contemplates substances made from the amorphous drug beads which may be flowable. Accordingly, a variety of administration routes are available. The particular mode selected will depend, of course, upon the particular active drug selected, the severity of the disease state being treated, and the dosage required for therapeutic efficacy. The amorphous drug beads described herein can be administered by any route, including without limitation, oral, buccal, sublingual, rectal, parenteral, topical, inhalational, injectable, transdermal, intravenous, intramuscular, nasal, via implant, transmucosal, ocular, pulmonary, intraperitoneal, intrathecal, or parenteral routes.

Using the present invention with any of the above routes of administration or dosage forms can be performed using well-known procedures and techniques available to one of ordinary skill in the art.

Preferred, non-limiting examples of oral dosage forms useful according to the present invention include capsules, gelatin capsules, caplets, cachets, tablets, bi-layer tablets, suspensions in aqueous liquors or non-aqueous liquids, a syrup, an elixir, an emulsion, powders, granules, dispersible granules, lozenges, or chewable lozenges, each containing a predetermined amount of the amorphous active drug. The oral dosage form may be administered to a patient once, twice, or thrice daily.

The present invention also contemplates the use of pharmaceutically acceptable carrier(s) which may be prepared from a wide range of materials. Without being limited thereto, such materials include diluents, binders and adhesives, lubricants, plasticizers, disintegrants, colorants, bulking substances, flavorings, sweeteners, humectants, and miscellaneous materials such as buffers and adsorbents in order to prepare a particular medicated composition.

In a preferred embodiment, the pharmaceutically acceptable carrier is a diluent, which may be selected from a wide range of materials such as calcium phosphate, calcium sulfate, carboxymethylcellulose calcium, microcrystalline cellulose, cellulose acetate, dextrates, dextrin, dextrose, fructose, glyceryl palmitostearate, hydrogenated vegetable oil, kaolin, lactitol, lactose, magnesium carbonate, magnesium oxide, maltitol, maltodextrin, maltose, polymethacrylates, powdered cellulose, pregelatinized starch, silicified microcrystalline cellulose, sodium chloride, sorbitol, starch, sucrose, sugar spheres, and talc, as well as other conventional diluents known to those skilled in the art.

Exemplary non-limiting binders which may be useful according to the present inventive subject matter may be selected from a wide range of materials such as acacia; alginic acid; hydroxypropylmethylcellulose, hydroxyethylcellulose, hydroxypropylcellulose, ethylcellulose, methylcellulose, carboxymethyl cellulose, or other suitable cellulose derivatives; dextrin; gelatin; glucose; hydrogenated vegetable oil; magnesium aluminum silicate; maltodextrin; polyethylene oxide; povidone; acrylic and methacrylic acid co-polymers; pharmaceutical glaze; sodium alginate; gums such as guar gum; and milk derivatives such as whey, starches, and derivatives; as well as other conventional binders well known to persons skilled in the art. In a preferred embodiment, the binders useful according to the present inventive subject matter are selected from the group consisting of hydroxypropylmethylcellulose, ethylcellulose, povidone, acrylic, methacrylic acid copolymers, pharmaceutical glaze, gums, milk derivatives, and mixtures thereof.

Exemplary non-limiting lubricants which may be useful according to the present inventive subject matter may be selected from a wide range of materials such as calcium stearate, canola oil, glyceryl palmitostearate, hydrogenated vegetable oil, magnesium oxide, mineral oil, poloxamer, polyethylene glycol, polyvinyl alcohol, sodium benzoate, sodium lauryl sulfate, sodium stearyl fumarate, stearic acid, talc, and zinc stearate, as well as other conventional lubricants well known to persons skilled in the art.

Exemplary non-limiting plasticizers which may be useful according to the present inventive subject matter may be selected from a wide range of materials such as lanolin, mineral oil, petrolatum, benzyl phenylformate, chlorobutanol, diethyl phthalate, glycerol, polyethylene glycol, propylene glycol, sorbitol, and triacetin, as well as other conventional plasticizers well known to persons skilled in the art.

Exemplary non-limiting disintegrants which may be useful according to the present inventive subject matter may be selected from a wide range of materials such as alginic acid, carboxymethylcellulose, hydroxypropylcellulose, microcrystalline cellulose, colloidal silicon dioxide, croscarmellose sodium, crospovidone, magnesium aluminum silicate, methylcellulose, povidone, sodium alginate, sodium starch glycolate, and starch, as well as other conventional disintegrants well known to persons skilled in the art.

Exemplary non-limiting colorants which may be useful according to the present inventive subject matter may be selected from a wide range of materials such as curcumin, lactoflavin (riboflavin), tartrazine, quinoline yellow, sunset yellow FCF, cochineal carminic acid, carmoisine, ponceau 4R, patent blue V, indigo carmine, chlorophylls, lissamine green, caramel, black PN, carbo medicinalis vegetabilis, carotenoids, xanthophylls, betanin, anthocyanins, calcium carbonate, titanium dioxide, iron oxides and hydroxides, indigotine, alphazurine FG, indanthrene blue, fast green FCF, alizarin cyanine, quinizarine green SS, pyranine concentrated, orange II, dibromofluorescein, diiodofluorescein, erythrosine, ponceau SX, lithol rubin B, toney red, tetrabromofluorescein, eosine, tetrachlorotetrabromofluorescein, phloxine B, helindone pink CN, brilliant lake red R, acid fuchsine, lake bordeaux B, flaming red, alba red, allura red AC, alizurol purple SS, tartrazine, sunset yellow FCF, fluorescein, naphthol yellow S, uranine, quinoline yellow, alumina, aluminum powder, annatto extract, betacarotene, bismuth oxychloride, bronze powder, calcium carbonate, canthaxanthin, chromium-cobalt-aluminum oxide, chromium hydroxide green, cochineal extract, copper powder, dihydroxy acetone, ferric ammonium citrate, ferric ammonium ferrocyanide, ferric ferrocyanide, guanine, iron oxides synthetic, logwood extract, mica, potassium sodium copper chlorophyllin, pyrogallol, pyrophyllite, talc, and zinc oxide, as well as other conventional colorants well known to persons skilled in the art.

Exemplary non-limiting bulking substances which may be useful according to the present inventive subject matter may be selected from a wide range of materials such as sugar, lactose, gelatin, starch, and silicon dioxide, as well as other conventional bulking substances well known to persons skilled in the art.

Exemplary non-limiting flavorings which may be useful according to the present inventive subject matter may be selected from a wide range of materials such as ethyl maltol, fructose, maltol, tartaric acid, ethyl vanillin, fumaric acid, malic acid, menthol, vanillin, peppermint, and oil of wintergreen or cherry, as well as other conventional flavorings well known to persons skilled in the art.

Exemplary non-limiting sweeteners which may be useful according to the present inventive subject matter may be selected from a wide range of materials such as acesulfame potassium, aspartame, dextrose, fructose, liquid glucose, glycerol, lactitol, lactose, maltitol, maltose, saccharin, saccharin sodium, sodium cyclamate, sorbitol, sucrose, confectioner's sugar, and xylitol, as well as other conventional sweeteners well known to persons skilled in the art.

Exemplary non-limiting humectants which may be useful according to the present inventive subject matter may be selected from a wide range of materials such as glycerin, propylene glycol, sorbitol, and triacetin, as well as other conventional humectants well known to persons skilled in the art.

Exemplary non-limiting solvents which may be useful according to the present inventive subject matter are water, ethanol, isopropyl alcohol, methylene chloride, or mixtures and combinations thereof, as well as other conventional solvents well known to persons skilled in the art.

The following example is illustrative of a preferred embodiment of the invention and is not to be construed as limiting the invention thereto. All percentages given throughout the specification are based upon weight unless otherwise indicated.

EXAMPLES

Example 1

The following example demonstrates the enhanced dissolution of the present inventive amorphous drug beads.

Quantities of Itraconazole and Pluronic™ F68 in a ratio of 9 parts Itraconazole to 1 part Pluronic™ F68 were melted separately in an oil bath. Once both components were completely melted, they were combined, emulsified with high shear, and poured onto a cold plate to cool rapidly. The resulting material was tested for dissolution, the results of which are shown in FIG. 1.

As can be seen from FIG. 1, a dissolution rate of almost 100% was achieved with the amorphous drug beads according to the present inventive subject matter. In contrast, crystalline Itraconazole (control) only resulted in a dissolution rate of 20% over the same time period.

The invention being thus described, it will be obvious that the same may be varied in many ways. Such variations are not to be regarded as a departure from the spirit scope of the invention and all such modifications are intended to be included within the scope of the following claims.

I claim:

1. A method of making an amorphous drug bead, the method comprising: a) providing an amorphous active drug; b) melting said amorphous active drug; c) forming a droplet from said melted amorphous active drug; and d) quenching said droplet in a liquid organic surfactant; wherein said droplet immediately solidifies when quenched in said liquid organic surfactant, said liquid organic surfactant having a lower melting point than said amorphous active drug; wherein said amorphous drug bead has a particle size of about 1 to about 50 microns.

2. The method of claim 1, wherein said organic surfactant coats said amorphous active drug.

3. The method of claim 1, wherein said organic surfactant has a melting point above room temperature.

4. The method of claim 1, wherein said organic surfactant has a melting point above 40.degree. C.

5. The method of claim 1, wherein said amorphous drug beads have a particle size of about 5 to about 45 microns.

6. The method of claim 1, wherein said amorphous drug beads are flowable.

7. The method of claim 1, wherein said amorphous active drug is 4-[4-[4-[4-[[2-(2,4-Dichlorophenyl)-2-(1H-1,2,4-triazol-1-ylmethyl)-1,3-d- ioxolan-4-yl]methoxy]phenyl]-1-piperazinyl]phenyl]-2,4-dihydro-2-(1-methy- 1 propyl)-3H-1,2,4-triazol-3-one or a pharmaceutically acceptable salt thereof.

8. The method of claim 1, wherein said organic surfactant is selected from the group consisting of polymers, low molecular weight oligomers, natural products, gelatin, casein, lecithin (phosphatides), gum acacia, cholesterol, tragacanth, stearic acid, benzalkonium chloride, calcium stearate, glyceryl monostearate, cetostearl alcohol, cetomacrogol emulsifying wax, sorbitan esters, polyoxyethylene alkyl ethers, macrogol ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol, polyvinylpyrrolidone, dextran, lecithin, organic solvents, and mixtures thereof.

9. The method of claim 1, wherein said organic surfactant is nonionic or anionic.

* * * * *